United States Patent
Sevenster

(10) Patent No.: US 11,990,226 B2
(45) Date of Patent: May 21, 2024

(54) ADVANCED LOOP SELECTION SYSTEMS AND METHODS FOR SUPPORTING EFFICIENT ECHO COMPARISON

(71) Applicant: KONINKLIJKE PHILIPS N.V., Eindhoven (NL)

(72) Inventor: Merlijn Sevenster, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 531 days.

(21) Appl. No.: 17/267,955

(22) PCT Filed: Aug. 27, 2019

(86) PCT No.: PCT/EP2019/072757
§ 371 (c)(1),
(2) Date: Feb. 11, 2021

(87) PCT Pub. No.: WO2020/043684
PCT Pub. Date: Mar. 5, 2020

(65) Prior Publication Data
US 2021/0216812 A1    Jul. 15, 2021

Related U.S. Application Data

(60) Provisional application No. 62/723,678, filed on Aug. 28, 2018.

(51) Int. Cl.
*G06K 9/62* (2022.01)
*G06F 18/22* (2023.01)
(Continued)

(52) U.S. Cl.
CPC ............ *G16H 30/40* (2018.01); *G06F 18/22* (2023.01); *G06F 18/40* (2023.01); *G16H 50/70* (2018.01)

(58) Field of Classification Search
CPC ........ G16H 30/40; G16H 50/70; G06F 18/22; G06F 18/40; G06K 9/62
(Continued)

(56) References Cited

U.S. PATENT DOCUMENTS

| 7,634,121 B2 | 12/2009 | Novatzky |
| 8,060,178 B2 | 11/2011 | Zhou |

(Continued)

FOREIGN PATENT DOCUMENTS

| CA | 2901830 | * | 9/2014 | ........... G06V 10/774 |
| JP | 2008526420 | * | 7/2008 | ............... G06T 7/38 |

(Continued)

OTHER PUBLICATIONS

International Search Report and Written Opinion dated Dec. 11, 2019 For International Application No. PCT/EP2019/072757 Filed Aug. 27, 2019.

*Primary Examiner* — Jerome Grant, II

(57) ABSTRACT

A system and method for selecting image sequences of echocardiogram studies for visual comparison by a user. The method includes receiving image sequences from a current study and a prior study to be compared. The method includes determining a relevant view of the image sequences of the current and prior studies and selecting an image sequence from one of the current and prior studies to a user via an interactive comparison panel. The method includes determining which image sequence of the relevant view of an other of the current and prior studies that most closely matches the selected image sequence via the interactive comparison panel.

17 Claims, 5 Drawing Sheets

(51) Int. Cl.
*G06F 18/40* (2023.01)
*G16H 30/40* (2018.01)
*G16H 50/70* (2018.01)

(58) Field of Classification Search
USPC .......................................................... 382/128
See application file for complete search history.

(56) References Cited

U.S. PATENT DOCUMENTS

| | | |
|---|---|---|
| 8,891,881 B2 | 11/2014 | Gupta |
| 2016/0012319 A1 | 1/2016 | Mabotuwana |
| 2016/0063727 A1 * | 3/2016 | Gao ....................... G06V 10/50 382/103 |
| 2016/0232658 A1 | 8/2016 | Syeda-Mahmood |
| 2018/0108125 A1 | 4/2018 | Beymer |
| 2018/0286503 A1 | 10/2018 | Sevenster |

FOREIGN PATENT DOCUMENTS

| | | | | |
|---|---|---|---|---|
| KR | 101912570 | * | 10/2018 | ............... G06N 3/04 |
| WO | 2010029470 A1 | | 3/2010 | |
| WO | 2018/095792 | | 5/2018 | |

* cited by examiner

ADVANCED LOOP SELECTION SYSTEMS AND METHODS FOR SUPPORTING EFFICIENT ECHO COMPARISON

CROSS REFERENCE TO RELATED APPLICATIONS

This application is the U.S. National Phase application under 35 U.S.C. § 371 of International Application No. PCT/EP2019/072757 filed Aug. 27, 2019, which claims the benefit of U.S. Provisional Patent Application No. 62/723,678 filed Aug. 28, 2018. These applications are hereby incorporated by reference herein.

BACKGROUND

An echocardiogram is routinely used in the diagnosis and treatment of patients with different heart diseases. In some cases, the cardiologist may be required to compare a current echocardiogram study with a previous echocardiogram study for a patient. A typical echocardiogram acquisition, however, may result in multiple image acquisitions of the same view due to, for example, subtle differences (e.g., at different depths) or because the quality of initial acquisitions was considered non-diagnostic or non-optimal. Thus, the cardiologist may be presented with a large number of image sequences to review during a comparison of current and previous studies, resulting in a time-consuming and inefficient process.

SUMMARY

The exemplary embodiments are directed to a method, comprising: receiving image sequences from a current study and a prior study to be compared, each of the image sequences including data corresponding to a view of the image sequence; determining a relevant view of the image sequences of the current and prior studies; selecting an image sequence of a relevant view of one of the current and prior studies for comparison; displaying the image sequence from one of the current and prior studies to a user via an interactive comparison panel; determining which image sequence of the relevant view of an other of the current and prior studies most closely matches the selected image sequence; and displaying the image sequence from the other of the current and prior studies that most closely matches the selected image sequence via the interactive comparison panel.

The exemplary embodiments are directed to a system, comprising: a non-transitory computer readable storage medium storing an executable program; and a processor executing the executable program to cause the processor to: receive image sequences from a current study and a prior study to be compared, each of the image sequences including data corresponding to a view of the image sequence; determine a relevant view of the current and prior studies; select an image sequence of the relevant view of one of the current and prior studies for comparison; display the image sequence from one of the current and prior studies to a user via an interactive comparison panel; determine which image sequence of the relevant view of an other of the current and prior studies most closely matches the selected image sequence; and display the image sequence from the other of the current and prior studies that most closely matches the selected image sequence via the interactive comparison panel.

The exemplary embodiments are directed to a non-transitory computer-readable storage medium including a set of instructions executable by a processor, the set of instructions, when executed by the processor, causing the processor to perform operations, comprising: receiving image sequences from a current study and a prior study to be compared, each of the image sequences including data corresponding to a view of the image sequence; determining a relevant view of the current and prior studies; selecting an image sequence of the relevant view of one of the current and prior studies for comparison; displaying the image sequence from one of the current and prior studies to a user via an interactive comparison panel; determining which image sequence of the relevant view of an other of the current and prior studies most closely matches the selected image sequence; and displaying the image sequence from the other of the current and prior studies that most closely matches the selected image sequence via the interactive comparison panel.

DETAILED DESCRIPTION

Figure 1:
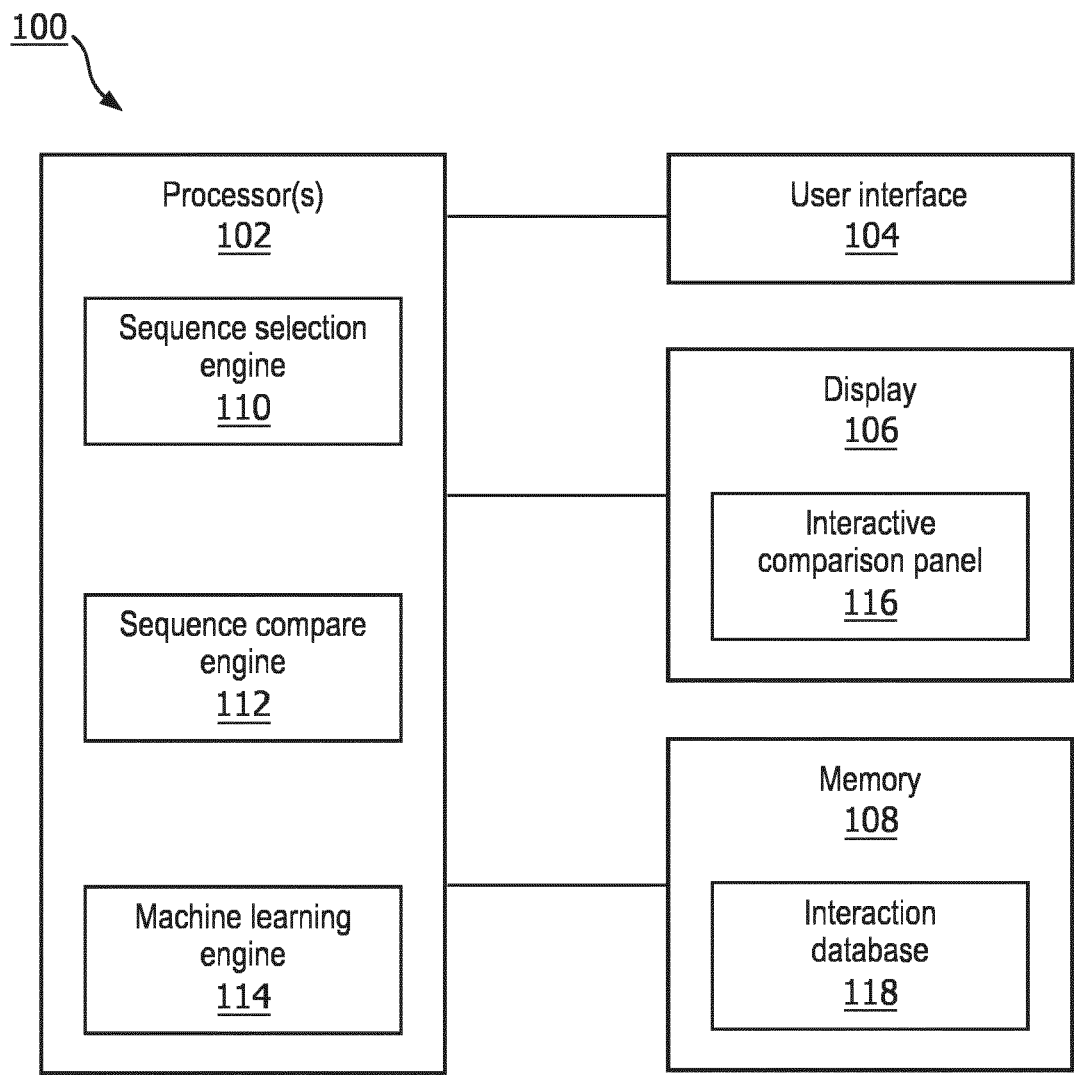
FIG. 1 shows a schematic drawing of a system according to an exemplary embodiment.

The exemplary embodiments may be further understood with reference to the following description and the appended drawings, wherein like elements are referred to with the same reference numerals. The exemplary embodiments relate to systems and methods for selecting image sequences of relevant views of current and prior echocardiogram studies to be visually compared by a user. Selected image sequences from each of the relevant views are presented to the user in an interactive comparison panel so that the user may further select which sequences, from the current and prior studies, that the user wishes to visually compare. Those sequences which the system determines are most likely to be selected by the user for visual comparison may be presented to the user in the interactive comparison panel. The user, however, may select any of the available sequences for visual comparison. These user selections may then be stored and used to improve the sequence selection process so that only the most relevant and/or most likely to be selected sequences are presented to subsequent users of the interactive comparison panel.

As will be described in greater detail below, the exemplary embodiments improve the operation of the system in multiple manners. In a first example, the storage of the user selections to improve the sequence selection process increases the speed at which relevant sequences are displayed to the user and decreases search time for the relevant sequences. In another example, as will be described in greater detail below, context and other information is stored with the sequences allowing for more efficient storage and searching of the sequences, thereby improving system performance.

As shown in FIG. 1, a system 100, according to an exemplary embodiment of the present disclosure, selects image sequences of current and prior echocardiogram studies to be visually compared by a user (e.g., cardiologist), presenting sequences of the most relevant views to the user in the context of a comparison indication. The comparison indication may include a condition or anatomy that is being compared such as, for example, left ventricle performance or mitral regurgitation. The system 100 comprises a processor 102, a user interface 104, a display 106, and a memory 108. The processor 102 may include a sequence selection engine 110, a sequence compare engine 112, and a machine learning engine 114. An interactive comparison panel 116 showing the image sequences of the current and prior studies available to be visually compared is displayed on the display 106. Using the user interface 104, the user may select image sequences from the interactive comparison panel 116 for visual comparison.

The sequence selection engine 110 receives a series of echocardiogram image sequences from a current study and selects one or more sequences from the current study, which the sequence selection engine 110 deems is most likely to be selected for visual comparison by the user. The user may then select the image sequence(s) selected by the sequence selection engine 110 or select a different image sequence from the current study for visual comparison. The sequence compare engine 112 then selects the image sequence(s) from the prior study that most closely matches the image sequence(s) selected by the user. Again, the user may select the image sequence(s) selected by the sequence compare engine 112 or select a different image sequence for visual comparison to the user-selected image sequence(s) of the current study. All of these user-system interactions, along with context information, are stored to an interaction database 118 of the memory 108. The information stored in the interaction database may be used via the machine learning engine 114 to create models for improving the sequence selecting process of the sequence selection engine 110 and/or the sequence compare engine 112 based on previous user selections.

It will be understood by those of skill in the art, that although the exemplary embodiments show and describe the sequence selection engine 110 as selecting image sequence(s) from a current study, the sequence selection engine 110 may similarly select image sequence(s) from the prior study, with the sequence compare engine 112 selecting image sequence(s) from the current study which most closely match the selected sequences from the prior study. It will also be understood by those of skill in the art that the image sequences of the current and prior studies may be accessed from a patient's medical record, which may be stored to the memory 108.

The interactive comparison panel 116 may show all of the available image sequences of the current and prior studies, indicating which of the image sequences from the current and prior studies are most likely to be chosen by the user for visual comparison. In particular, in one embodiment involving the interactive comparison panel 116, the image sequences most likely to be chosen by the user for visual comparison may be based on the comparison indication indicated and/or selected by the user. For example, image sequences selected by the sequence selection engine 110 and the sequence compare engine 112 may be highlighted on the display 106. Alternatively, as more user-system interaction data is stored to the interaction database 118 so that the sequence selection engine 110 and the sequence compare engine 112 are able to run a model created by the machine learning engine 114 to better predict the image sequences from the current and prior studies that would be selected by the user for visual comparison, the interactive comparison model 116 may display only those image sequences that are most likely to be selected by the user.

Those skilled in the art will understand that the engines 110-114 may be implemented by the processor 102 as, for example, lines of code that are executed by the processor 102, as firmware executed by the processor 102, as a function of the processor 102 being an application specific integrated circuit (ASIC), etc.

Figure 2:
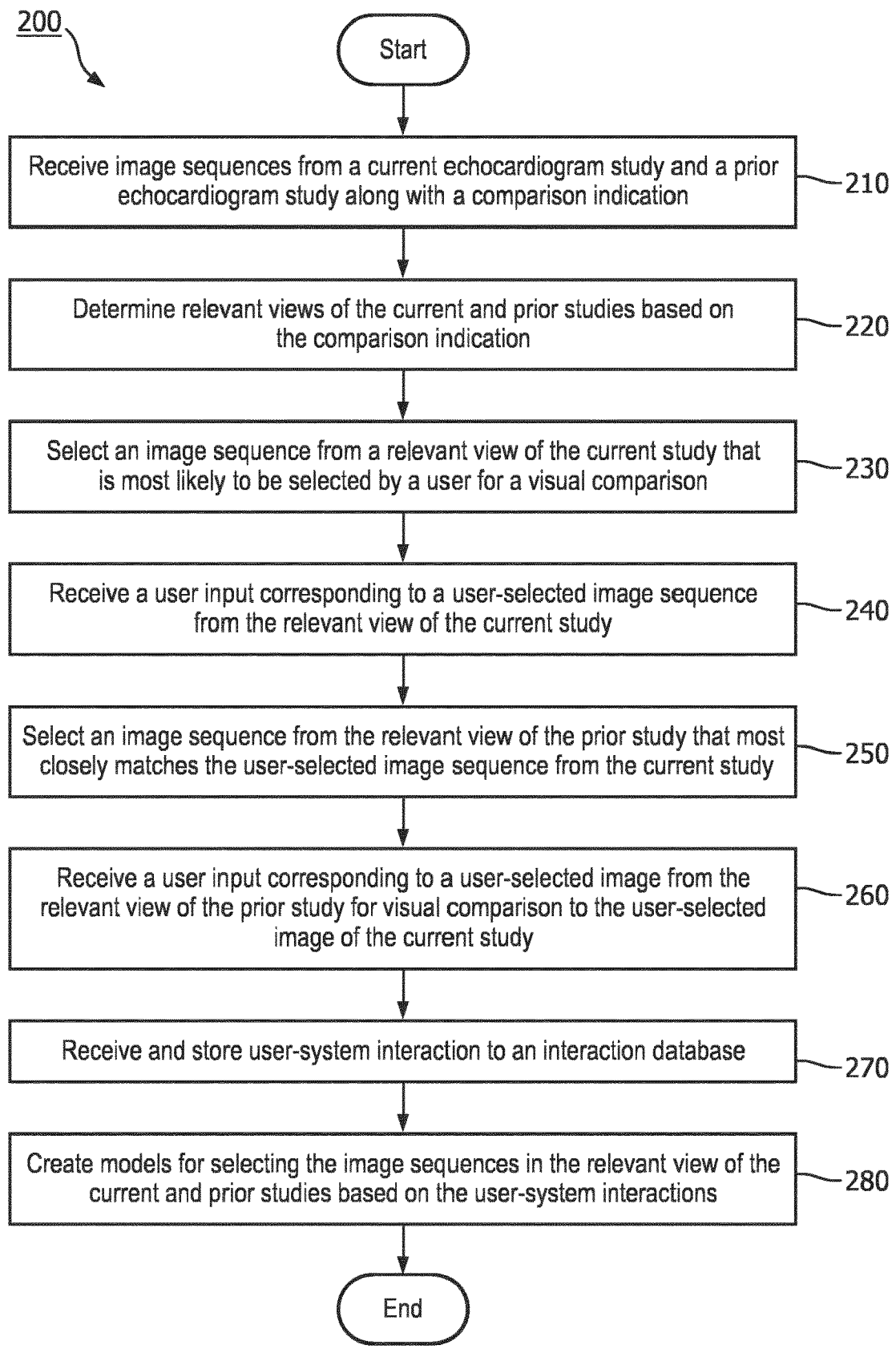
FIG. 2 shows a flow diagram of a method according to an exemplary embodiment.

FIG. 2 shows an exemplary method 200 for selecting image sequences of current and prior echocardiogram studies to be visually compared by the user and presenting sequences of the most relevant views to the user in the context of the comparison indication. In 210, the sequence selection engine 110 receives image sequences from current and prior echocardiogram studies along with a structural comparison indication from the user. The sequences from the echocardiogram studies may be retrieved from patient medical records (e.g., Picture Archiving and Communication System). The structural comparison indication may be input by the user via the user interface 104 and may include indications such as, for example, "compare LV performance" or "compare mitral regurgitation". In 220, the sequence selection engine 110 determines relevant views of the echocardiogram studies which show the comparison indication input via the user in 210. The sequence selection engine 110 may determine, for example, that the PLAX, SLAX, AP2 and AP4 views show LV performance. The echocardiogram views that show the comparison indication may be determined via, for example, a look-up table.

In 230, the sequence selection engine 110 selects one or more image sequences of the relevant views of the current echocardiogram study, which is most likely to be selected by the user for visual comparison. The sequence selection engine 110 processes the sequences of the relevant views including contextual information including, for example, an order of the sequences (based on an acquisition timestamp) and the indication, to generate an output for each sequence in the relevant views, representing the likelihood of the sequence being selected by the user for visual comparison. The output may be a binary yes or no, or a number in a predetermined range (e.g., 0-1) with high numbers representing a high likelihood of being selected and low numbers representing a low likelihood of being selected. The sequence selection engine 110 may run one or multiple mathematical, statistical or rule-based prediction models. The sequence selection engine 110 may make use of known and proprietary image feature libraries. A rule-based technique, for example, may execute high level reasoning such as:

If the sequence is first in the series of more than one of the same view, assign it output 0.
If the sequence is last in the series, apply prediction model X.

In another example, particularly during earlier iterations of the method 200, the rule-based technique may, by default, select the last sequence in each view as most likely to be selected by the user for visual comparison since in many cases sequences are imaged until an optimal sequence has been obtained. In yet another example, the prediction model may take the order of the image sequence into account. For example, the prediction model may consider that a sequence is fourth in a sequence of five sequences. The selected image sequence(s) of the current study is displayed to the user in the interactive comparison panel 116.

In 240, the processor 102 receives a user input selecting one or more sequences of a relevant view of the current echocardiogram study that the user would like to view for comparison. The user may select sequences that are different than the image sequences selected by the sequence selection engine 110 in 230. The user may input the user selection via the user interface 104.

In 250, the sequence compare engine 112 selects one or more sequences from the prior study that closely matches the sequences selected by the user in 240. The sequence compare engine 112 compares each of the image sequences from the same relevant view of the prior study to the user-selected image sequence of the current study and assigns each of the image sequences of the same relevant view of the prior study a score (e.g., between 0-1) to mark their similarity. In one exemplary embodiment, the sequence compare engine 112 may execute a difference operation on the frames of the sequences being compared and produces a weighted differed score across all frames. In another exemplary embodiment, the sequence compare engine 112 may first register the heartbeats of the sequences before taking the difference of the frames, potentially leveraging the ECG signal recorded along with the sequence image data in a dedicated DICOM field. In yet another exemplary embodiment, the sequence compare engine 112 may first reduce the resolution before taking the difference of the frames. Once the image sequence(s) of the prior study matching the user-selected sequence is determined, the matching image sequences(s) is displayed to the user via the interactive comparison panel 116.

In 260, the processor 102 receives a user input selecting a sequence of the prior study to be visually compared to the user-selected sequence of the current study in 240. The user selection may be made via the user interface 104. As will be described in further detail below, upon selection of an image sequence from the prior study, the user may provide further input indicating a desire to view the selected image sequence of the current study, in 240, and the selected image sequence of the prior study, in 260, side-by-side for visual comparison.

Although 230 and 240 describe selecting image sequences from a current study and 250 and 260 describe selecting image sequences from a prior study, it will be understood by those of skill in the art that the sequence selector engine 110 may similarly select image sequences from a prior study so that the sequence compare engine 112 selects a matching image sequence from the current study. It will also be understood by those of skill in the art that 230-260 may be repeated as necessary to select image sequences from the current and prior studies for each of the different relevant views, if desired.

In 270, all of the user-system interactions are received from the interactive comparison panel 116 and stored to the interaction database 118. For example, the sequences selected by the sequence selector engine 110 and the sequence compare engine 112, the user-selected sequences, and any contextual information (e.g., sequence order, structural comparison indication) may be stored to the interaction database 118. Although the user-system interaction is shown and described as being stored in 270, it will be understood by those of skill in the art that the user-system interactions, along with any contextual information of the sequences, may be stored to the interaction database 118 as they occur. In particular, the interactions may be stored to the interaction database 118 as the information is received from the interactive comparison panel.

In 280, the machine learning engine 114 accesses the interaction database 118 to create machine learning, statistical and/or rule-based models for inclusion in the sequence selection engine 110 and the sequence compare engine 112. For creating a model for the sequence selection model, for example, the machine learning engine 114 may use information such as a series of image sequences, the one or more sequences that were selected (ground truth), an order of sequences, and a comparison indication. For creating a model for the sequence compare engine 112, the machine learning engine 114 may use information such as two series of sequences that were compared (image data), one or more selected sequences in the first series of sequences (ground truth), an order of both sequences, and a comparison indication.

A model for each of the sequence selector engine 110 and the sequence compare engine 112 may be created using techniques, such as convolutional neural networks, Random Forest, Support Vector Machine, logistics regressions, making use of known or new image processing feature libraries, aiming to maximize performance of predicting the ground truth sequence from among the other sequences. According to a further exemplary embodiment, the model creation engine may also make use of a view detection engine, which determines the view (e.g., PLAX, SLAX, AP2, AP3, AP4) of a sequence—i.e., a position of a probe relative to the heart. The machine learning engine 114 may be called according to a predetermined schedule or, alternatively, manually via a system administrator. For example, the machine learning engine 114 may be called every night or every month to improve models for the sequence selection engine 110 and the sequence compare engine 112. In a further embodiment, a fixed set of annotated instances may be used to track the performance of the newly created to determine whether performance of the new model is superior to the model currently being used. If performance is determined to be superior, the model currently being used may be replaced by the newly created model.

Figure 3:
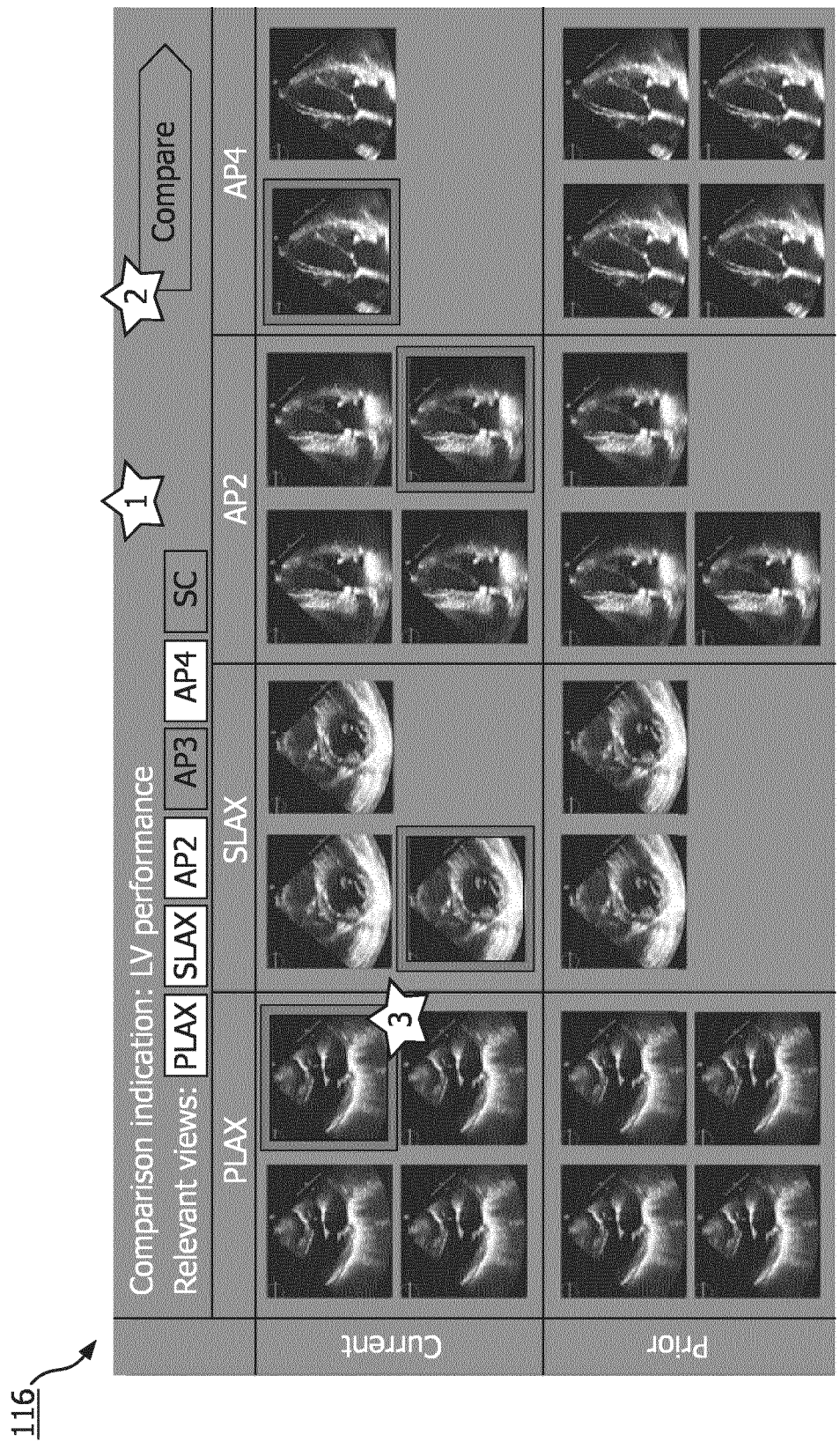
FIG. 3 shows an exemplary comparison panel comparing relevant views of a current and a prior echocardiogram study, with sequences of the current study that are considered to be most likely to be selected for visual comparison by the user being highlighted, according to an exemplary embodiment.
Figure 4:
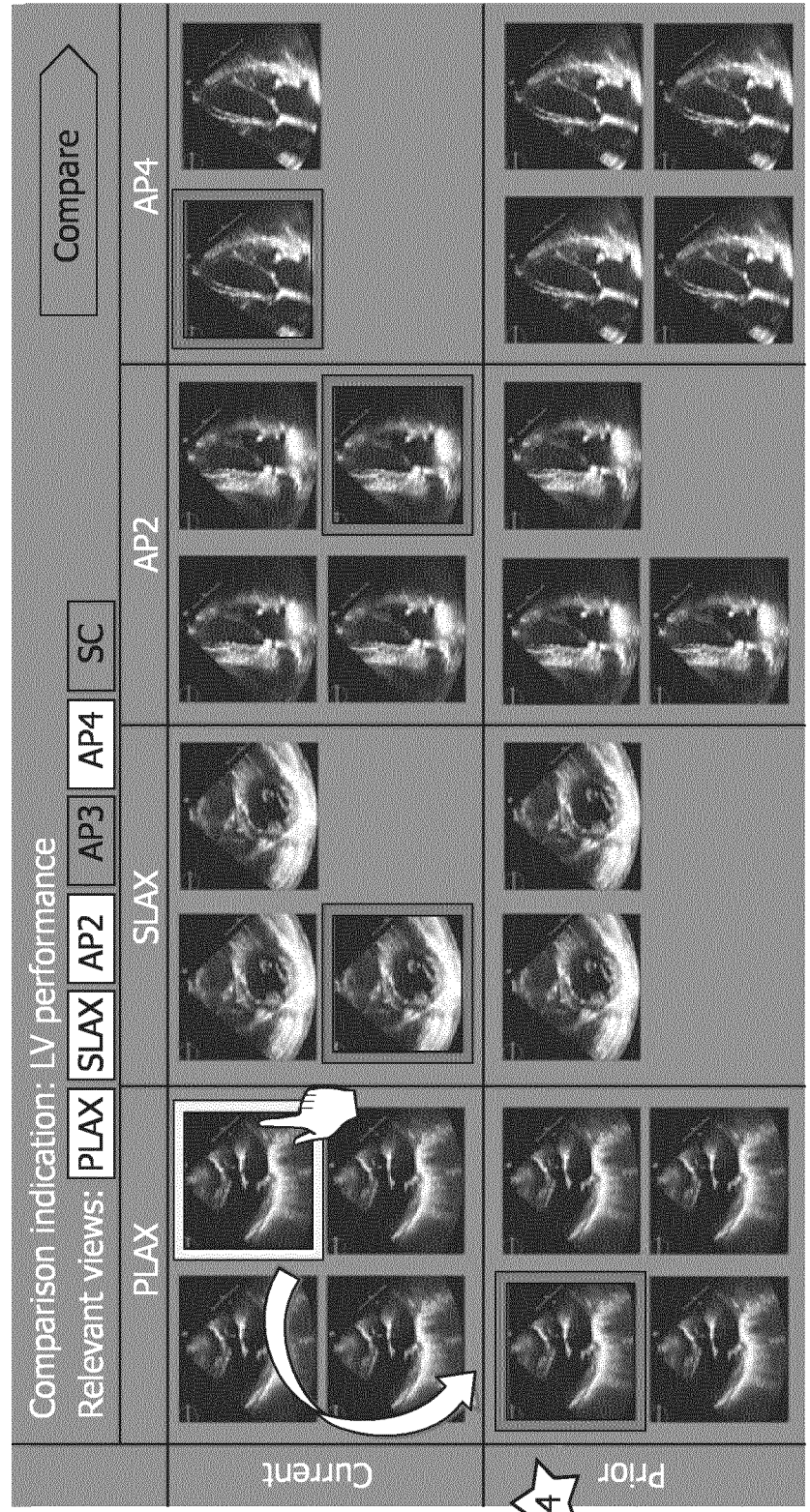
FIG. 4 shows the exemplary comparison panel of FIG. 3, wherein selection of a sequence of the current study for visual comparison by the user results in highlighting of a matching sequence in the prior echocardiogram study, according to an exemplary embodiment.
Figure 5:
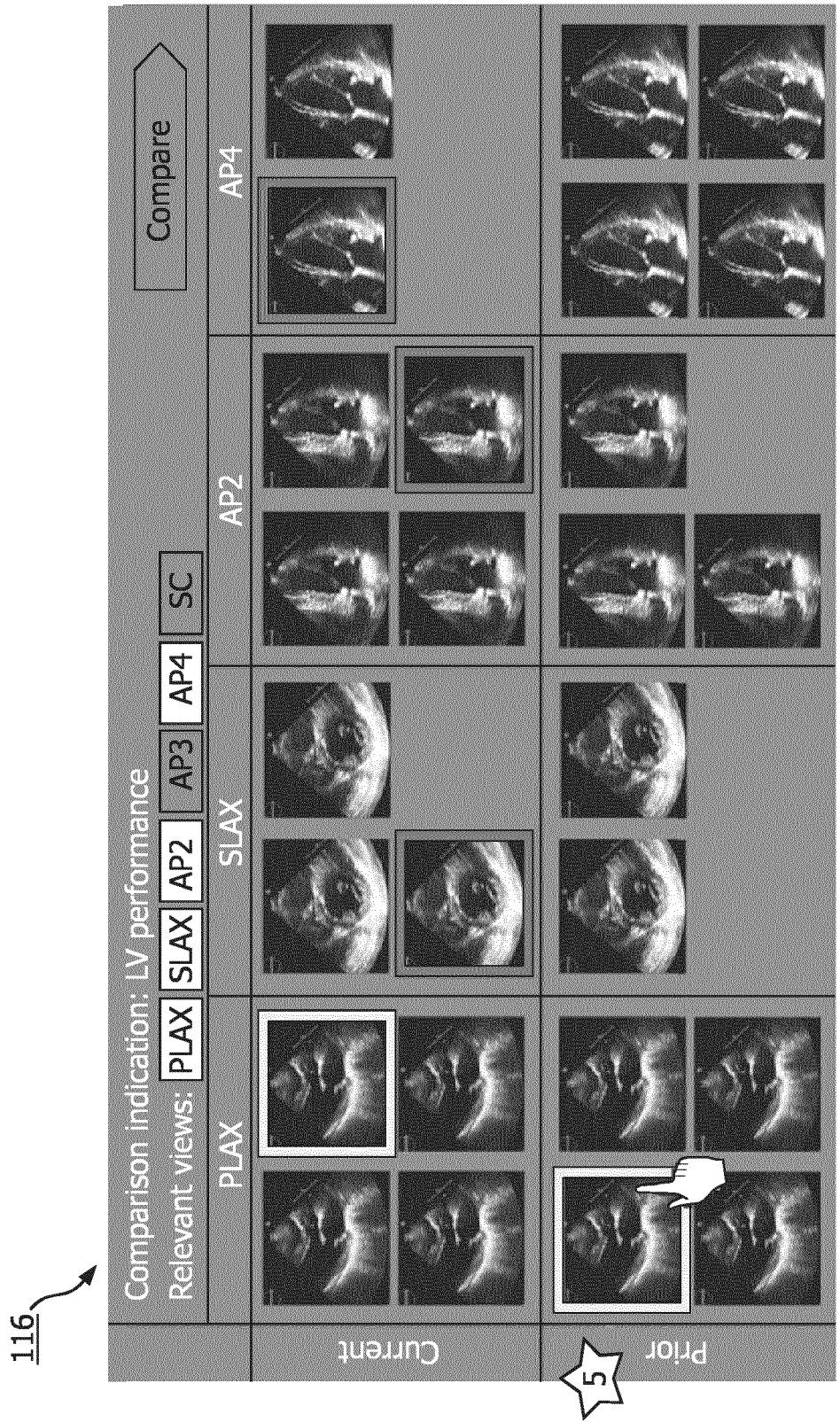
FIG. 5 shows the exemplary comparison panel of FIGS. 3 and 4, wherein the user selects a matching sequence of the prior echocardiogram study for visual comparison with the selected sequence of the current echocardiogram study, according to an exemplary embodiment.

FIGS. 3-5 show an exemplary interactive comparison panel according to the system 100 and the method 200. As shown in FIG. 3, the interactive comparison panel 116 shows sequences in each of the relevant views of both the current echocardiogram study and the prior echocardiogram study according to the structural comparison indication received by the sequence selector engine 110 in 210. For example, for an LV performance indication in which the relevant views are determined to be the PLAX, SLAX, AP2 and AP4 views in 220, the interactive comparison panel 116 shows sequences from the current study and the prior study in each of the relevant views, disabling other views that are deemed irrelevant. The interactive comparison panel 116, however, allows other views to be easily enabled by the user, if so desired. Similarly, the interactive comparison panel allows enabled views to be easily disabled, if desired.

The interactive comparison panel 116 of FIG. 3 shows all the available sequences in each of the relevant views for the current and prior studies, with the sequences in the current study that are selected by the sequence selector engine 110 in 230 being highlighted on the display 106. The highlighting provides an indication to the user of which sequences were determined to be the most-likely to be selected by the user for visual comparison. Although the exemplary embodiment shows the selected sequence as being highlighted, it will be understood by those of skill in the art that the interactive comparison panel 116 may use other methods for indicating selection by the sequence selector engine 110. In addition, although FIG. 3 only shows sequences of the current study as being selected by the sequence selector engine 110, the interactive comparison panel 116 may also be figured to highlight sequence selections from the prior study or both the current and prior studies.

Although the interactive comparison panel 116 of FIG. 3 shows all the available sequences for each of the relevant views, in another embodiment, the interactive comparison model 116 may only show those sequences that have been selected by the sequence selector engine 110 as being most likely to be selected by the user for visual comparison in 230. In this embodiment, the interactive comparison panel 116 is not required to highlight (or provide any other indication of selection) any sequences since only those sequences that have been selected are shown. Alternatively, the interactive comparison model may show any sequence generating an output that is above a predetermined threshold value, highlighting the sequence having the highest generated output.

As discussed above, the user may select the sequence selected by the sequence selector engine 110 or, alternatively, choose to select a different sequence. In the example shown in FIG. 4, the user selects a sequence of the current study that is highlighted—i.e., selected by the sequence selector engine 110—in one of the relevant views (e.g., PLAX). Selecting the sequence causes a sequence in that same view of the prior study to become highlighted. This highlighted sequence shows the sequence determined by the sequence compare engine 112 as most closely matching the user-selected sequence in 2650. As shown in FIG. 5, the user may then select the sequence from the prior study which the user would like to visually compare to the user-selected sequence of the current study. Upon selection of the two sequences which the user would like to compare, the user may press, for example, a compare button of the interactive comparison panel to generate a side-by-side visual comparison of the two selected sequences.

Those skilled in the art will understand that the above-described exemplary embodiments may be implemented in any number of manners, including, as a separate software module, as a combination of hardware and software, etc. For example, the sequence selection engine 110, the sequence compare engine 112 and the machine learning engine 114 be programs containing lines of code that, when compiled, may be executed on the processor 102.

It will be apparent to those skilled in the art that various modifications may be made to the disclosed exemplary embodiments and methods and alternatives without departing from the spirit or scope of the disclosure. Thus, it is intended that the present disclosure cover the modifications and variations provided that they come within the scope of the appended claims and their equivalents.

What is claimed is:

1. A computer-implemented method for selecting image sequences of echocardiogram views of current and prior echocardiogram studies to be visually compared by a user, comprising:
receiving image sequences from each of a current echocardiogram study and a prior echocardiogram study to be compared, each of the image sequences including data corresponding to a view of the image sequence;
receiving a comparison indication from a user, wherein the comparison indication includes a condition or anatomy that is being compared;
determining the echocardiogram views of the image sequences of the current and prior studies which show the comparison indication;
selecting an image sequence of the echocardiogram view of one of the current and prior studies for comparison;
displaying the image sequence from one of the current and prior studies to a user via an interactive comparison panel;
determining which image sequence of the echocardiogram view of an other of the current and prior studies most closely matches the selected image sequence;
displaying the image sequence from the other of the current and prior studies that most closely matches the selected image sequence via the interactive comparison panel; and
receiving a user input corresponding to a matching image sequence selected by the user for visual comparison to the selected image sequence.

2. The method of claim 1, further comprising receiving a user input corresponding to the selected image sequence.

3. The method of claim 1, further comprising creating at least one of a machine learning, statistical and rule-based model for selecting the image sequence from one of the current and prior and for determining the image sequence from the other of the current and prior studies that most closely matches the selected image sequence.

4. The method of claim 1, wherein selecting the image sequence from the one of the current and prior studies includes analyzing an order of acquisition of each of the image sequences of the one of the current and prior studies.

5. The method of claim 1, wherein selecting the image sequence from the one of the current and prior studies includes generating an output for each image sequence of the one of the current and prior studies corresponding to a likelihood the sequence will be selected by the user for visual comparison.

6. The method of claim 5, wherein image sequences of the one of the current and prior studies having outputs greater than a predetermined value are displayed via the interactive comparison panel.

7. The method of claim 1, wherein determining which image sequence of the echocardiogram view of an other of the current and prior studies most closely matches the selected image sequence includes outputting a score for each image sequence of the other of the current and prior studies in the relevant view corresponding to a level of similarity between each image sequence of the other of the current and prior studies and the selected image sequence.

8. The method of claim 7, wherein image sequences of the other of the current and prior studies having an output score greater than a predetermined value are displayed via the interactive comparison panel.

9. A non-transitory computer-readable storage medium including a set of instructions executable by a processor, the set of instructions, when executed by the processor, causing the processor to perform operations as claimed in claim 1.

10. A system, comprising:
a non-transitory computer readable storage medium storing an executable program; and
a processor executing the executable program to cause the processor to:

receive image sequences from each of a current echocardiogram study and a prior echocardiogram study to be compared, each of the image sequences including data corresponding to a view of the image sequence;

receive a comparison indication from a user, wherein the comparison indication includes a condition or anatomy that is being compared;

determine an echocardiogram view of the current and prior studies which show the comparison indication;

select an image sequence of the echocardiogram view of one of the current and prior studies for comparison;

display the image sequence from one of the current and prior studies to a user via an interactive comparison panel;

determine which image sequence of the echocardiogram view of an other of the current and prior studies most closely matches the selected image sequence; and display the image sequence from the other of the current and prior studies that most closely matches the selected image sequence via the interactive comparison panel.

11. The system of claim 10, wherein the processor executes the executable program to cause the processor to:
receive a user input corresponding to the selected image sequence.

12. The system of claim 10, wherein the processor executes the executable program to cause the processor to:
receiving a user input corresponding to a matching image sequence selected by the user for visual comparison to the selected image sequence.

13. The system of claim 10, wherein the processor executes the executable program to cause the processor to:
create at least one of a machine learning, statistical and rule-based model for selecting the image sequence from one of the current and prior studies and for determining the image sequence from the other of the current and prior studies that most closely matches the selected image sequence based on user-system interactions.

14. The system of claim 10, wherein selecting the image sequence from the one of the current and prior studies includes an order of image acquisition of each of the one of the image sequences of the one of the current and prior studies.

15. The system of claim 10, wherein selecting the image sequence from the one of the current and prior studies includes generating an output for each image sequence of the one of the current and prior studies corresponding to a likelihood the sequence will be selected by the user for visual comparison.

16. The system of claim 15, wherein image sequences of the one of the current and prior studies having outputs greater than a predetermined value are displayed via the interactive comparison panel.

17. The system of claim 10, wherein determining which image sequence of the relevant view of an other of the current and prior studies most closely matches the selected image sequence includes outputting a score for each image sequence of the other of the current and prior studies in the relevant view corresponding to a level of similarity between each image sequence of the other of the current and prior studies and the selected image sequence.

* * * * *